United States Patent [19]

Brown

[11] Patent Number: 4,975,237
[45] Date of Patent: Dec. 4, 1990

[54] DYNAMIC LIGHT SCATTERING APPARATUS

[75] Inventor: Robert G. W. Brown, Worcester, England

[73] Assignee: The Secretary of State for Defence in Her Britannic Majesty's Government of the United Kingdom of Great Britain and Northern Ireland, London, England

[21] Appl. No.: 380,438

Related U.S. Application Data

[63] Continuation of PCT GB88/000124, filed Feb. 12, 1988.

[22] Filed: Jul. 17, 1989

[30] Foreign Application Priority Data

Mar. 12, 1987 [GB] United Kingdom ............... 8705844

[51] Int. Cl.$^5$ ........................................... G01N 21/51
[52] U.S. Cl. ..................................... 356/338; 356/339
[58] Field of Search ............................... 356/338, 339

[56] References Cited

U.S. PATENT DOCUMENTS 4,150,360  4/1979  Koop et al. .
4,762,413  8/1988  Namba et al. ..................... 356/339

FOREIGN PATENT DOCUMENTS 0106684  4/1984  European Pat. Off. .
2122034  8/1972  France .

OTHER PUBLICATIONS

Davi, "Application of a Laser Self-Beat Spectroscopic Techniques to the Study of Solutions of Human Plasma Liporoteins", *J. Chem. Soc. Faraday Trans II*, vol. 20, pp. 200–208, 1974.

Alou et al., "Improving Light Beating Experiments by Dust Discrimination", *Rev. Sci. Instrum.*, vol. 46, No. 4, pp. 388–390, 4/75.

"Fiber-Optical Quasi-Elastic Light Scattering of Concentrated Dispersions" by H. Auweter and D. Horn, *Journal of Colloid and Interface Science*, vol. 105, No. 2, Jun. 1985, pp. 399–409.

"Abrasion Tester of Test-Piece" *Patent Abstracts of Japan*, vol. 10, No. 358 (P-522) (2415) Dec. 2, 1986, and JP, A, 61–155837 (Toshiba Corp.), 15-07-1966, See Abstract.

*Primary Examiner*—Davis L. Willis
*Assistant Examiner*—Matthew W. Koren
*Attorney, Agent, or Firm*—Nixon & Vanderhye

[57] ABSTRACT

A dynamic light scattering apparatus (10) comprises a laser (12) optically coupled to a light scattering sample (26) via a first monomode optical fibre (18) and a first lens (22). The lens (22) produces a beam waist (24) in the sample (26), and scattered light is collected by a receive lens (30) and a second monomode optical fibre (34). The second fibre (34) has an end face in the Fourier plane (84) of the receive lens (30, 70), and defines an aperture matched to a single Airy disc (82) of the lens (30, 70). The receive fibre (34) accordingly receives a single spatial mode of light scattered from the sample (26), this mode corresponding to a single plane wave to which many scatterers contribute. The receive fibre (34) also attenuates unwanted spatial modes because of its monomode character. A photodetector (36) detects light transmitted by the receive fibre (34).

6 Claims, 10 Drawing Sheets

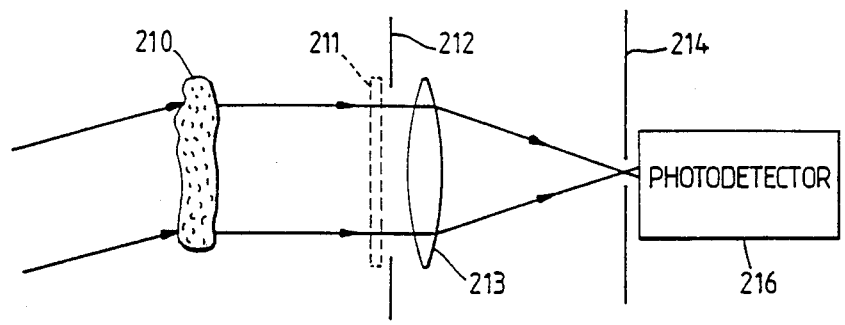
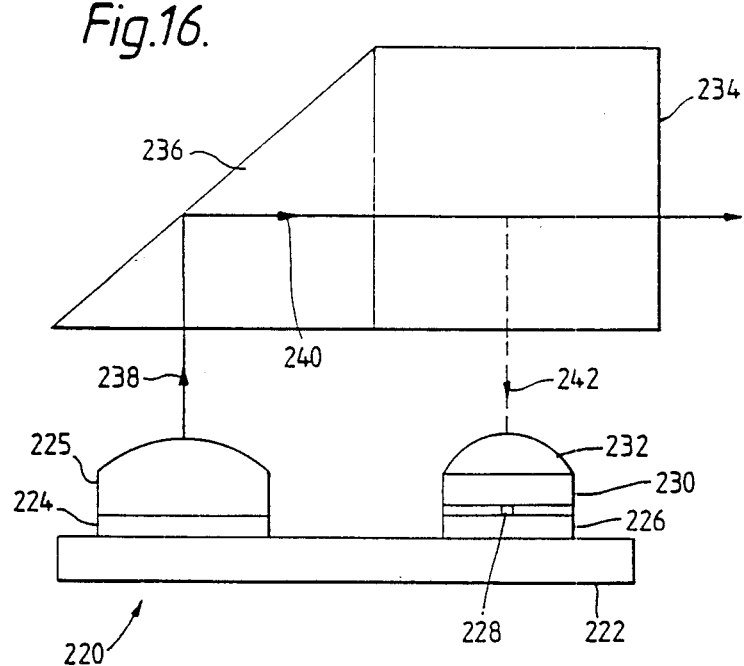

DYNAMIC LIGHT SCATTERING APPARATUS

This application is a continuing application under 35 USC 363 of International Application No. PCT/GB88/00124, filed Feb. 24, 1988.

This invention relates to a dynamic light scattering apparatus.

Dynamic light scattering measurement is a known technique for studying the hydrodynamic properties of fluids and particles suspended in fluids. It is used for studying dispersions of macromolecules in liquids and colloids, and particulate matter suspended in gases. Light such as a laser beam is incident on a particle suspension and undergoes Rayleigh or Mie scattering from the particles. The particles exhibit Brownian motion, and the scattered light intensity fluctuates with time in a manner which characterises particle motion. Measurement of this intensity fluctuation by known autocorrelation techniques permits determination of particle diffusion coefficient and hydrodynamic radius together with related information. Autocorrelation is described in British Patent No. 1,290,336.

Dynamic light scattering measurement embraces laser Doppler velocimetry (LDV) and anemometry (LDA), quasi-elastic light scattering (QELS), intensity fluctuation spectroscopy (IFS) and photon correlation spectroscopy (PCS). It has been the subject of considerable scientific research in recent years, one early paper appearing in "Dielectric and Related Molecular Processes", Vol. 2, Ed Mansel Davies, Specialist Periodical Report (London: The Chemical Society) pages 48–105, 1975, P. N. Pusey and J. M. Vaughan.

A typical commercially available apparatus for observing dynamic light scattering is type No. PCS 100 manufactured by Malvern Instruments Ltd, a British Company. It comprises a laser and a lens to focus the laser beam to a waist or minimum diameter. The waist is arranged to lie within a sample cell containing the particle suspension of interest. Light scattered by the suspension at a chosen angle is imaged by a lens on to an optical slit. The superimposition of the slit image on to the laser beam delimits or defines the volume from which scattered light is received. Light diverges from the slit to a far field region (with respect to the lens) at which an interference pattern of speckles is observed. A small aperture is located in this region, and scattered light passes through the aperture for detection by a photomultiplier. For Argon ion laser light ($\sim 0.5$ $\mu$m wavelength), the slit width and aperture diameter would be in the order of 100 $\mu$m 200 $\mu$m respectively. The distances between laser waist and lens and lens and slit are each in the order of 10 cm. The aperture is about 2 cm from the slit.

The aperture size is important in any light scattering measurement since it defines what is referred to as the "coherence area". Pusey et al referred to above describe the coherence area concept at p. 68. It arises from the following analysis. Light scattered from the delimited scattering volume at a specific angle is the resultant of a vector addition of individual amplitudes scattered by respective particles distributed throughout the volume. Each individual scattered amplitude has a respective phase, and vector addition contributes to the process of interference. Since the aperture has a finite size, light received at various points along its diameter will correspond to different scattering angles. The resultant amplitude summation will therefore differ at points along this diameter. If the diameter is sufficiently great, the range of angles accepted by the aperture allow uncorrelated resultants to be detected. The requirement set out by Pusey et al is that the phases of resultants accepted by the aperture differ by not more than $2\pi$. The aperture is then said to transmit a single coherence area corresponding to mutually correlated light contributions or resultants.

Light transmitted by the aperture is detected by a photomultiplier, the output of which is fed to an autocorrelation device. This device correlates the photomultiplier signal with a time-delayed version of itself to produce a normalised intensity autocorrelation function $g^{(2)}(\tau)$, where $\tau$ is the time delay. This function is the Fourier transform of the power spectrum, or intensity of frequency components, produced by the scattering suspension. Each scattered photon is Doppler-shifted in frequency from that of the laser in accordance with the velocity of the relevant scattering particle.

The relationships between the measured normalised intensity autocorrelation function $g^{(2)}(\tau)$, the normalised electric field or amplitude autocorrelation function $g^{(1)}(\tau)$ and the amplitude spectrum $n(\omega)$ of the scattered light is given in British Patent No. 1,290,336 as follows:

$$g^{(1)}(\tau) = \int n(\omega) \exp(-j2\pi\omega\tau) d\omega \qquad (1)$$

$$g^{(2)}(\tau) = 1 + |g^{(1)}(\tau)|^2 \qquad (2)$$

here $\omega$ is the radiation angular frequency.

The autocorrelation technique involves measurement of $g^{(2)}(\tau)$ for each of a range values of $\tau$. The results are subsequently analysed by a well known computational procedure to yield the diffusion coefficient of the suspended particles, from which their hydrodynamic radius may be deduced.

The value of $[g^{(2)}(\tau)-1]$ at $\tau=0$, i.e. zero delay, is an indication of the optical quality of a light scattering measurement apparatus. From Equation (2), it is equal to $|g^{(1)}(0)|^2$, which mathematically should be equal to unity as a consequence of normalisation. It may be said broadly speaking to correspond to a figure of merit or signal to noise ratio, and is obtained by extrapolation of an experimental graph of $g^{(2)}(\tau)$ versus $\tau$. In practice, typical values of $[g^{(2)}(0)-1]$ for commercial instruments are in the range 0.3 to 0.5. If extreme care is taken, a value of 0.7 may be approached, this being the theoretical limit for a conventional apparatus of the kind arranged to detect a single coherence area. See for example J. Phys. A, Vol. 3, L45, 1970, Jakeman et al. In Biopolymers, Vol. 15, pages 61–95 (1976), Jolly and Eisenberg mention precautions taken to maximise performance. The authors employed a goniometer mounting for the scattered light collection optics to permit measurements over a range of scattering angles. The laser and goniometer were mounted on adjacent marble slabs placed on rubber covered concrete pillars. The pillars were arranged on separate concrete bases supported on the sandy soil beneath the laboratory with an intervening layer of cork. These arrangments provided a very high degree of mechanical isolation. They also illustrate the difficulties associated with the use of conventional optical components in dynamic light scattering measurements. The optical system must be accurately aligned. It must subsequently be maintained substantially free of vibration so that spurious intensity fluctuations at the detector do not occur. Furthermore, the optical components must have scrupulously clean surfaces, and the optical path must be free of dust particles. Any dust particles in the light path create spurious light scattering which greatly affects measured results. These cleanliness and mechanical isolation criteria are very difficult to satisfy in apparatus typically in the order of a cubic metre in volume.

In efforts to overcome the disadvantages of conventional optical systems, various forms of dynamic light scattering apparatus based on optical fibres have been developed. In Rev. Sci. Instrum 54 (8), Aug. 1983, Haller et al describe a light scattering photometer for measuring intensity fluctuation as a function of scattering angle. Conventional optical components are used to relay a laser beam to the centre of a scattering cell. An angularly distributed array of lenses, slits and optical fibres is arranged around the cell to relay light to a detector. Each lens images the cell centre or scattering volume on to a respective slit, and light passing through each slit is collected by a respective multimode optical fibre and relayed to the detector. This arrangement has the advantage that atmospheric dust cannot affect scattered light once it is within a fibre. In addition, the fibre array is considerably more compact than the equivalent conventional optical system would be. However, Haller et al still require conventional optical components to relay laser light to the cell, and to collect scattered light for entry to the fibres.

A fibre-optic light scattering apparatus with further reduced dependence on conventional optics is described by Auweter and Horn in Journal of Colloid and Interface Science, Vol. 105, No. 2, June 1985 pages 399–409. Light from a laser is focussed by a lens on to one end of a multimode optical fibre connected to a first branch of an optical Y coupler. Light passes through the coupler to a second multimode optical fibre having one end immersed in the scattering suspension. Backscattered light returns along the second fibre to the coupler, where it is divided between coupler branches. Light coupled to a second coupler branch passes along a third multimode fibre and is output to a lens. The lens images light on to a pinhole 50 μm in diameter. Light passing through the pinhole is incident on a detector. The pinhole acts as a "coherence aperture" which restricts the number $N_{coh}$ of coherence areas reaching the detector.

Auweter and Horn observe that the signal to noise ratio in light beating experiments depends on Ncoh, which should be less than unity. This is equivalent to the criterion mentioned earlier that the aperture should only accept resultants differing in phase by less than $2\pi$. Auweter and Horn employ a value of $N_{coh}$ of 0.07 for the second optical fibre end immersed in water. This corresponds to a coherence aperture equal to only 1/14th of a coherence area maximum size. Since this value is very small they expected a good signal to noise ratio to result. They mention the alternative possibility of employing monomode fibres without a pinhole or coherence aperture, but point out that this would result in $N_{coh}$ being typically 0.68. They conclude that the combination of multimode optical fibres and a coherence aperture is a factor of ten better than the single mode or monomode equivalent.

Auweter and Horn also describe the use of heterodyne (strictly speaking homodyne) detection. Scattered light reaching the detector undergoes mixing with original or unscattered laser light acting as a local oscillator. Beat signals are accordingly produced. The original laser light arises from reflections at fibre ends and optical fibre imperfections. Heterodyne or homodyne detection is advantageous in light scattering measurements, since it can be shown that this results in improved statistical properties of the system and also reduced sensitivity to spurious scattering from bubbles in the liquid. It is however very difficult to perform this kind of measurement using a conventional (non-fibre) optical system; the optics required approach unmanageable proportions and exhibit extreme difficulty in obtaining and maintaining alignment.

The Auweter and Horn light scattering apparatus is a considerable improvement over the conventional optical equivalent. It provides greatly reduced bulk and cost. However, it remains subject to the limitations of conventional systems as regards the value of $[g^{(2)}(0)-1]$, being subject to the theoretical maximum value of 0.7.

It is an object of the present invention to provide an improved light scattering apparatus capable of providing an enhanced value of $[g^{(2)}(0)-1]$, and suitable for implementation with fibre optics.

The present invention provides a dynamic light scattering apparatus comprising a laser arranged to produce a laser beam in a fluid scattering volume, and means for collecting and detecting light scattered from the scattering volume, characterised in that the apparatus also includes means for spatially Fourier transforming light scattered from the scattering volume and for isolating a single spatial mode thereof for detection.

As will be described later in more detail, apparatus of the invention exhibits a theoretical maximum value of $[g^{(2)}(0)-1]$ of 1.0. Moreover, embodiments of the invention have routinely achieved values of 0.97 or better with only comparatively modest standards of experimental care. Such values are more than twice the equivalent of 0.4 for typical conventional optical systems, and nearly 40% better than their theoretical limit. The reason for this is as follows. Because conventional systems limit light gathering to a region less than or equal to a coherence area, they also limit the maximum number of scatterers which can contribute to the measured signal. The invention performs Fourier transformation on the scattered light and isolates a single spatial mode thereof. This mode corresponds to a single plane wave from the scattering volume to which all scatterers within the volume will contribute over a sufficiently long period of time. The statistical properties of the Fourier approach of the invention are fundamentally superior to the real imaging/coherence area arrangement of the prior art, and this manifests itself as a considerable theoretical and practical improvement in $[g^{(2)}(0)-1]$.

Scattered light may be Fourier transformed by focussing means such as a lens having an aperture in its Fourier plane matched in size to an Airy disc of the lens. The aperture may be an end face of monomode optical fibre, the fibre being arranged to attenuate unwanted spatial modes. This embodiment of the invention is particularly advantageous in that the fibre acts as a low pass spatial filter which compensates for spatial mode impurity in the laser beam and also for mismatching between the aperture and the lens Fourier plane. The fibre may be coupled to monomode fibre optic coupling means arranged to produce light beating between scattered and unscattered laser light. Despite the prior art of Auweter and Horn, which regards the use of monomode fibres as disadvantageous, it has been found that such fibres are ideally suited to light beating experiments. This is because a monomode fibre transmits light as a plane wave perpendicular to and propagating along the fibre axis. Accordingly, monomode fibre optic coupling means produces the ideal required for light beam heterodyne or homodyne mixing, this being the accurate superposition of two waves upon one another. In contradistinction, Auweter and Horn rely on multimode mixing, which cannot produce accurate superposition and is prone to inaccuracies due to mode mixing changes.

In an alternative embodiment, the invention provides a light scattering apparatus in which the laser and Fourier transforming and isolating means are produced by integrated techniques upon a single support. The support may also retain detecting means associated with the isolating means. This embodiment may comprises a laser of layer construction arranged on the support and surmounted by a lens. The Fourier transforming and isolating means may be a second lens having means such as an aperture in its Fourier plane for isolating a single spatial mode.

In order that the invention might be more fully understood embodiments thereof will now be described, with reference to the accompanying drawings, in which.

Figure 8:
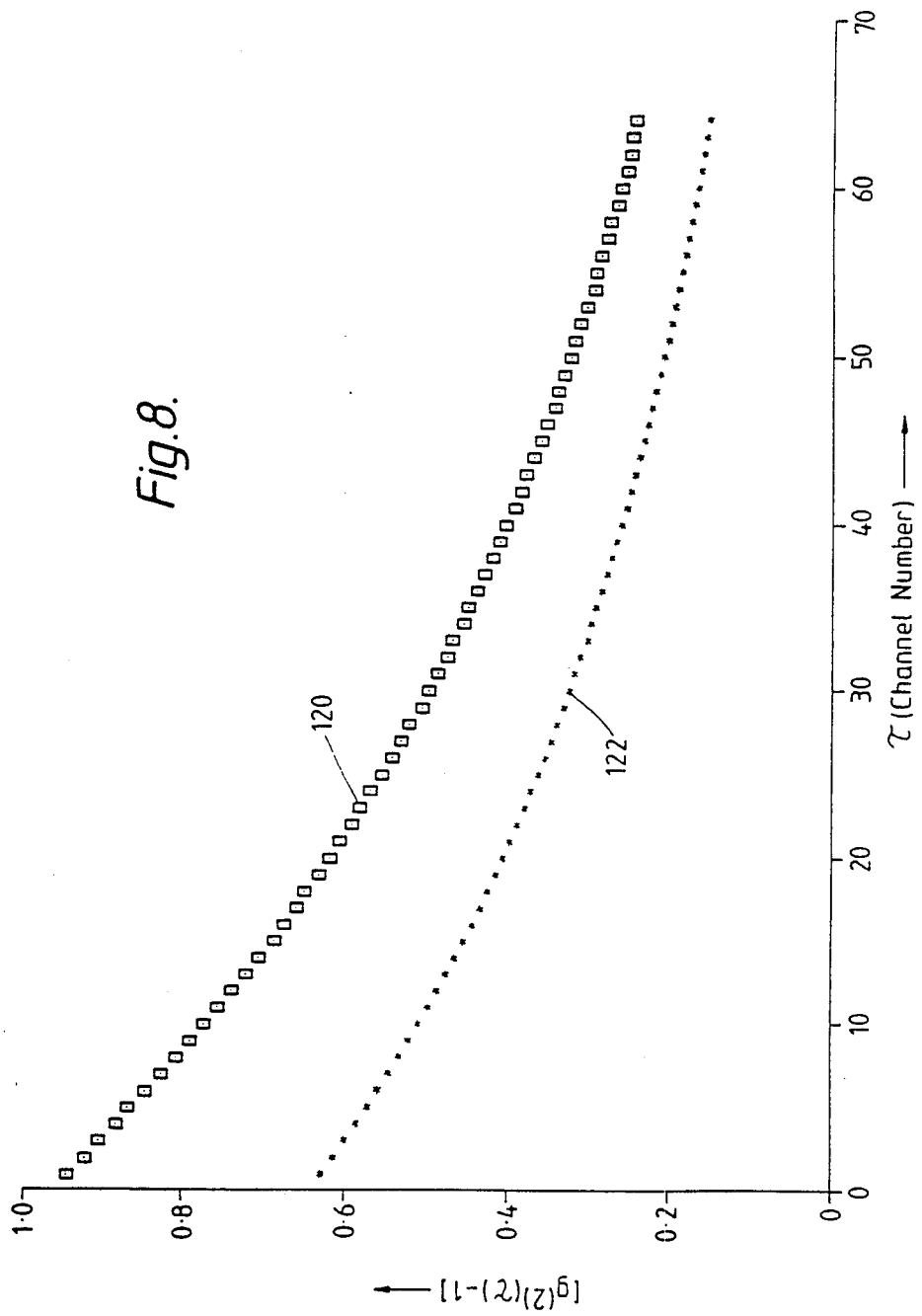
Figure 9:
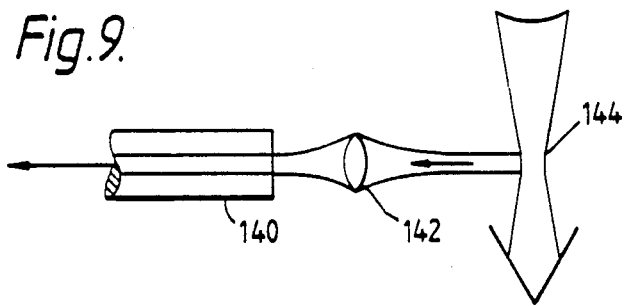
Figure 10:
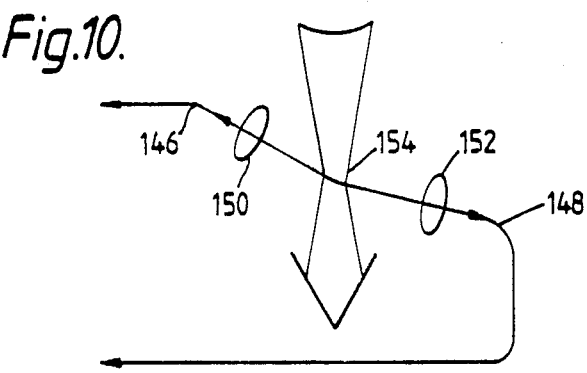
Figure 11:
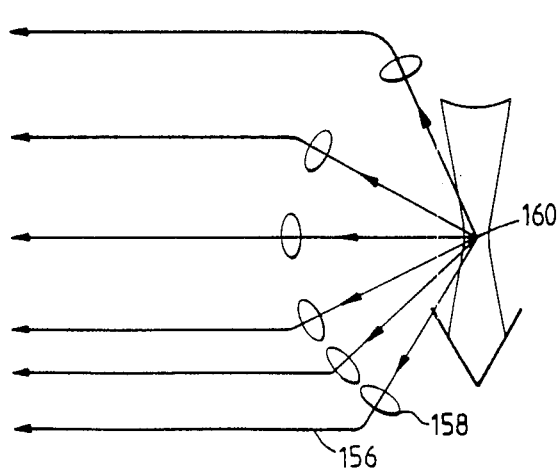
Figure 12:
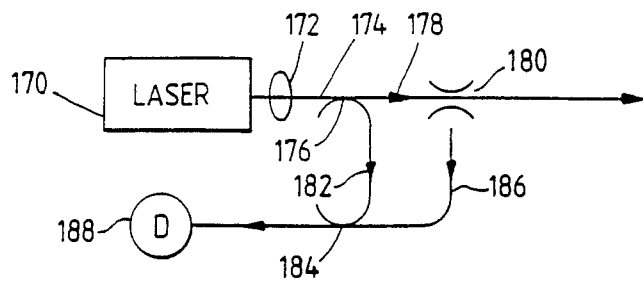
Figure 13:
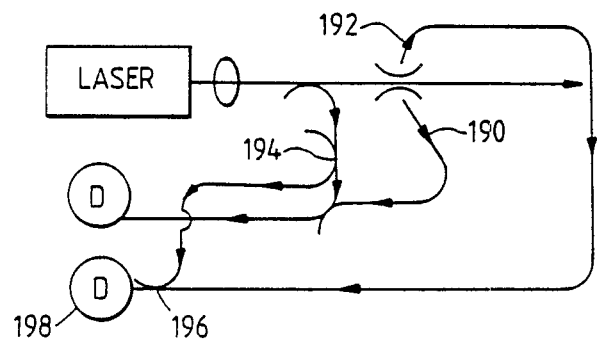
Figure 14:
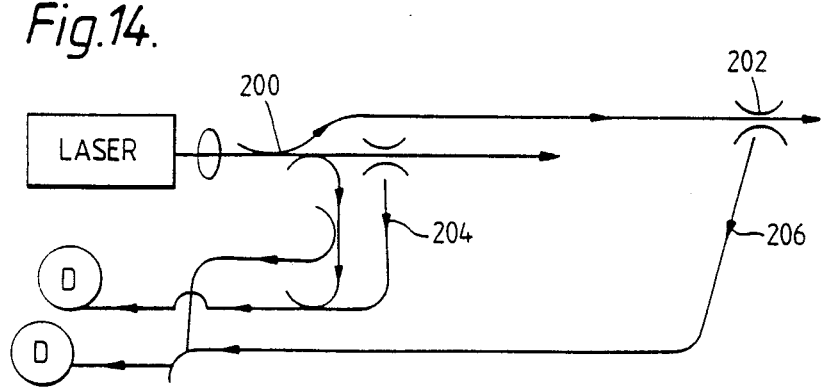
Figure 17:
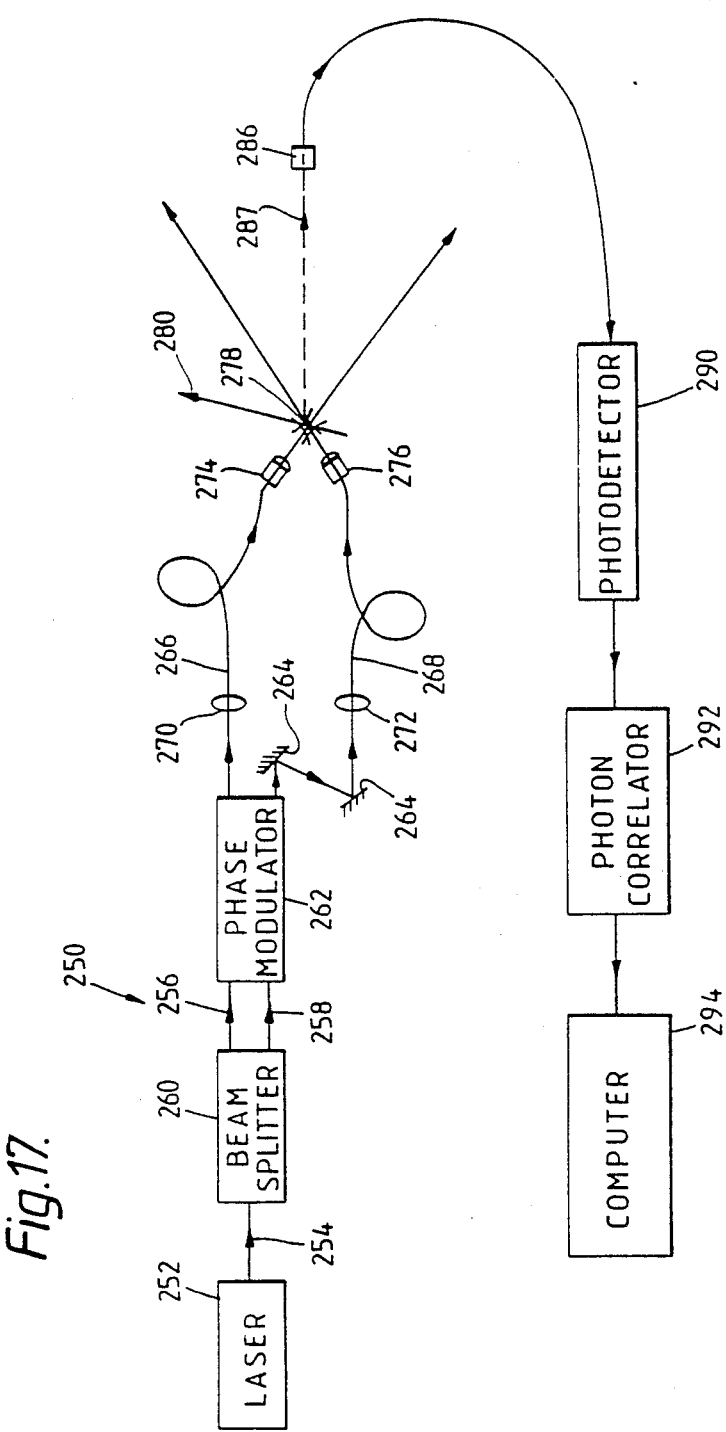

FIG. 8 provides plots of $[g^{(2)}(\tau)-1]$ against correlation time delay $\tau$ for an apparatus of the invention and for a prior art device;

FIGS. 9, 10 and 11 schematically show single-angle, two-angle and multi-angle light scattering arrangements of the invention respectively;

FIGS. 12, 13 and 14 schematically demonstrate homodyne light beating arrangements of the invention, and relate respectively to single angle, two-angle and two sample measurements;

FIG. 15 schematically illustrates an embodiment of the invention incorporating a pinhole aperture for spatial mode isolation;

FIG. 16 schematically shows an embodiment of the invention suitable for production by integrated techniques; and FIG. 17 schematically shows an embodiment of the invention arranged for laser Doppler difference velocimetry.

Figure 1:
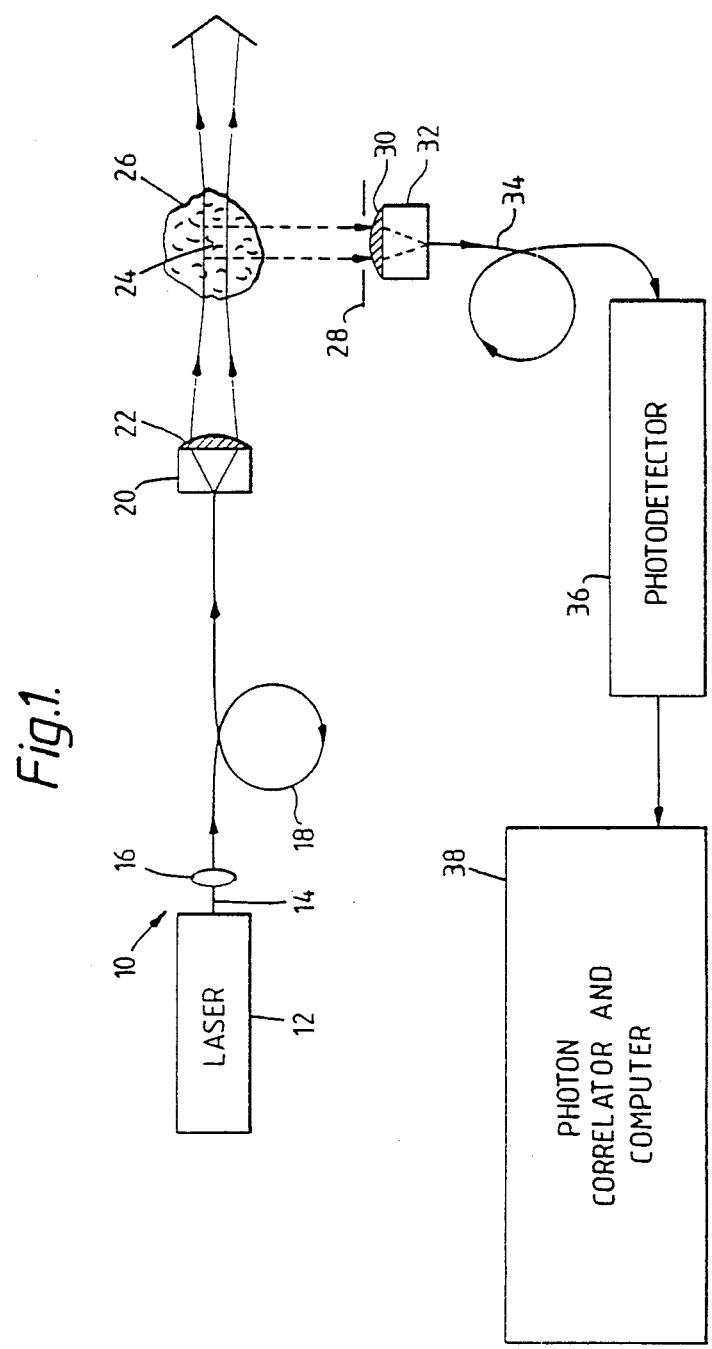
FIG. 1 is a schematic drawing of a dynamic light scattering apparatus of the invention.

Referring to FIG. 1, which is not to scale, there is shown a schematic drawing of a dynamic light scattering apparatus 10 of the invention. The apparatus 10 comprises a laser 12 emitting a light beam 14 which is launched by a microscope objective lens 16 into a monomode optical fibre 18. The fibre 18 terminates in a lens holder 20, the latter retaining a lens 22 producing a laser beam waist 24 within a light-scattering liquid 26. Light scattered at 90° C. to the undeflected laser beam passes via an aperture 28 to a second lens 30 mounted in a lens holder 32. A second monomode optical fibre 34 terminates in the back focal plane (not shown) of the second lens 30. As will be described later in more detail, the second fibre 34 defines an aperture in the Fourier plane of the lens 30. the aperture size being matched to the diameter of an Airy disc of the lens. The fibre 34 accordingly transmits a single spatial mode of scattered light corresponding to a single plane wave incident on the lens 30. Light transmitted by the fibre 34 passes to a photodetector 36. The end (not shown) of the fibre 34 is arranged in contact with or very close to the photodetector 36, no intervening aperture being required. Signals from the photodetector 36 pass to a photon correlator and computer system 38.

The operation of the apparatus 10 will now be briefly outlined, with a more detailed analysis being given later. Because the second fibre 34 collects light from the Fourier plane of the lens 30, it receives a proportion of the light scattered by all scatterers within the field of view of the lens 30. If the fibre 34 is arranged accurately on the optical axis of the lens 30, which is convenient but not essential, the fibre will receive only that light which is incident on the lens 30 as a plane wave perpendicular to the lens optical axis. In contradistinction, the prior art employs optical systems arranged to detect light from real images of the scattering volume. Moreover, the prior art restricts the size of the scattering volume, and hence also the number of scatterers, by limiting detection to a coherence area. A consequence of this is that the prior art is inferior in statistical terms, and has a maximum value of $[g^{(2)}(\tau)-1]$ at $\tau=0$ of 0.7, but more typically 0.4. An apparatus of the invention has proved to exhibit a value of this parameter in excess of 0.95, better than twice the typical prior art value and appreciably greater than the theoretical prior art limit.

Figure 2:
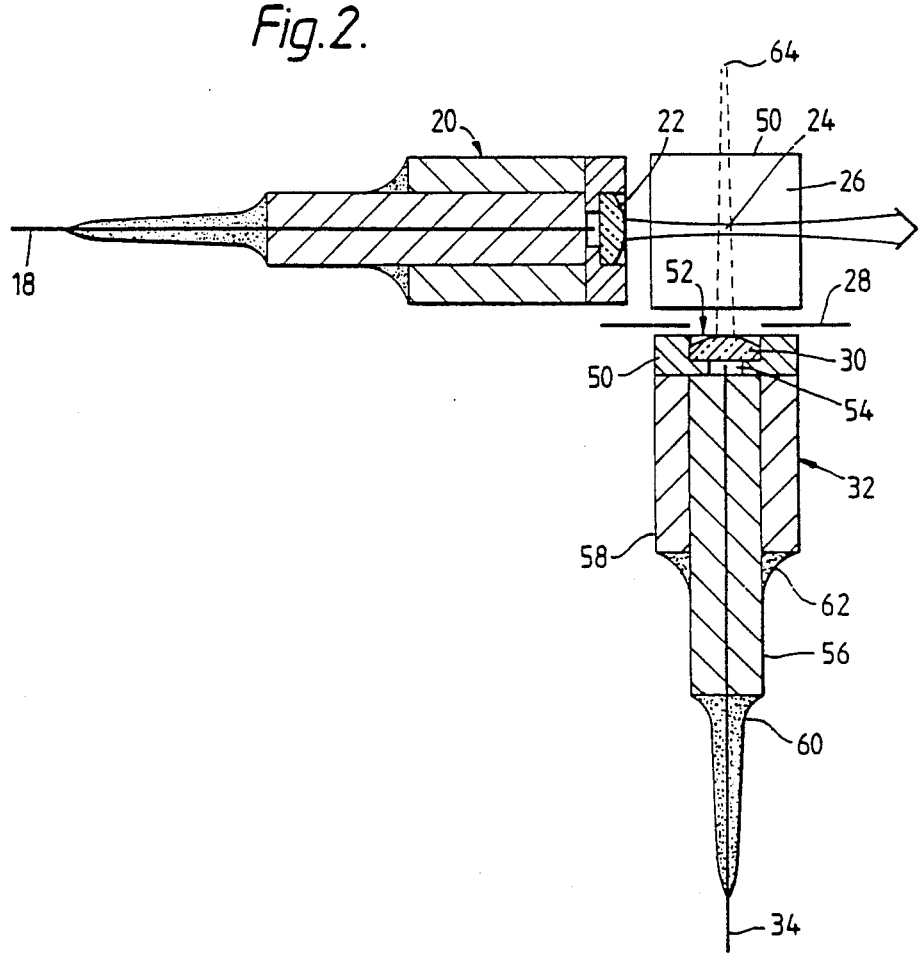
FIG. 2 is a sectional plan view of part of the apparatus of FIG. 1 shown in more detail to illustrate light input and output from a scattering volume.

Referring now to FIG. 2, in which parts previously described are like-referenced, there is shown a more detailed sectional plan view of the lens holders 20 and 32 and scattering liquid 26 of FIG. 1. The liquid 26 is retained within a square-section cell 50. The lens holders 20 and 32 are identical devices, the only difference between them other than manufacturing tolerances being the distance of the respective optical fibre 18 or 34 from the corresponding lens 22 or 30. Lens holder 32 will now be described. It comprises a lens mount 50 in the form of a brass plate with a recess 52 accommodating the lens 30. The recess 52 has a central hole 54 into which the optical fibre 34 is inserted, the fibre terminating at a distance from the lens equal to its focal length. The fibre 34 is a monomode fibre as has been said, and may be of the high birefringence (polarisation preserving) variety. It comprises a central glass core with a glass cladding and a surrounding polymer jacket, these being well-known features which are not illustrated. The polymer jacket is removed in the region of the fibre near and within the lens holder 32.

The fibre 34 is arranged within a fine bore capillary tube 56 itself slidable in a hole in a brass block 58. The fibre 34 emerges about 1 mm from the capillary bore end adjacent the lens 30. The lens-fibre separation is adjustable by sliding the tube 56 within the block 58. The fibre 34 is secured to the tube 56 by transparent glue 60 extending a short distance along the fibre length. The glue 60 reduces mechanical stress in the fibre 34 where it enters the tube 56. In addition the glue serves to extract light coupled to the fibre cladding, so-called cladding modes well known in the fibre optic art.

Once the fibre-lens separation has been adjusted accurately, as will be described later, the capillary tube 56 is bonded to the block 58 with epoxy resin adhesive 62.

Whereas, as has been said lens holder 20 produces a beam waist at 24 with cell 50, lens holder 32 would produce a more remote beam waist if laser light were input to it, as indicated by chain lines 64.

Figure 3:
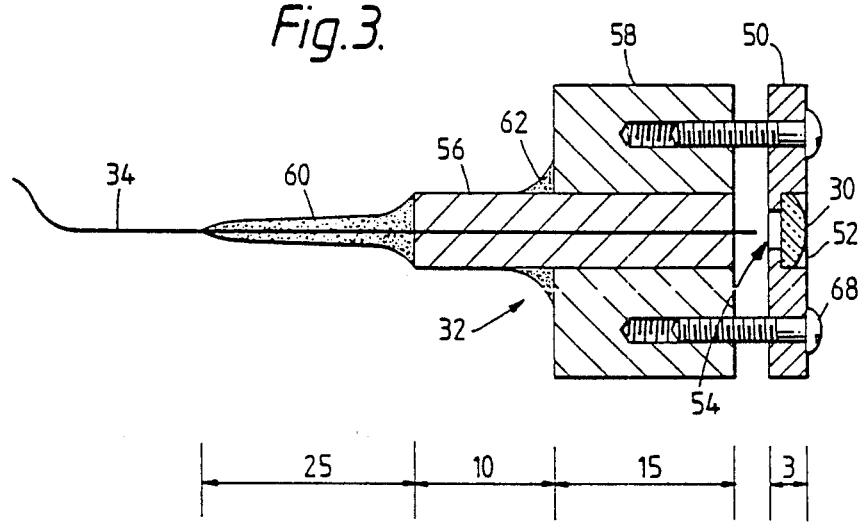
FIG. 3 is a sectional side view of a partly dissassembled lens holder of FIGS. 1 and 2.
Figure 4:
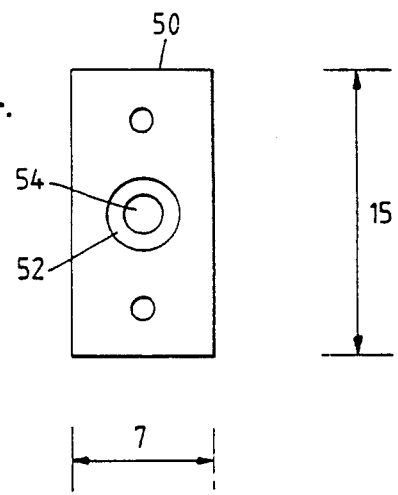
FIG. 4 is a schematic end view of the FIG. 3 lens holder.

Referring now to FIGS. 3 and 4, in which parts previously referred to are like referenced, there are shown respectively a sectional side view and a outline schematic end view of the lens holder 32. In FIG. 3, the lens mount 50 is shown prior to assembly and withdrawn from the block 58. The mount 50 and block 58 are secured together by screws 68. The dimensions of the parts in FIGS. 3 and 4 are as shown in millimetres, although the drawings are not accurately to scale. Moreover, the capillary tube 56 is shown having a surface flush with the block 58. This will not necessarily be the case after final adjustment to be described later.

Figure 5:
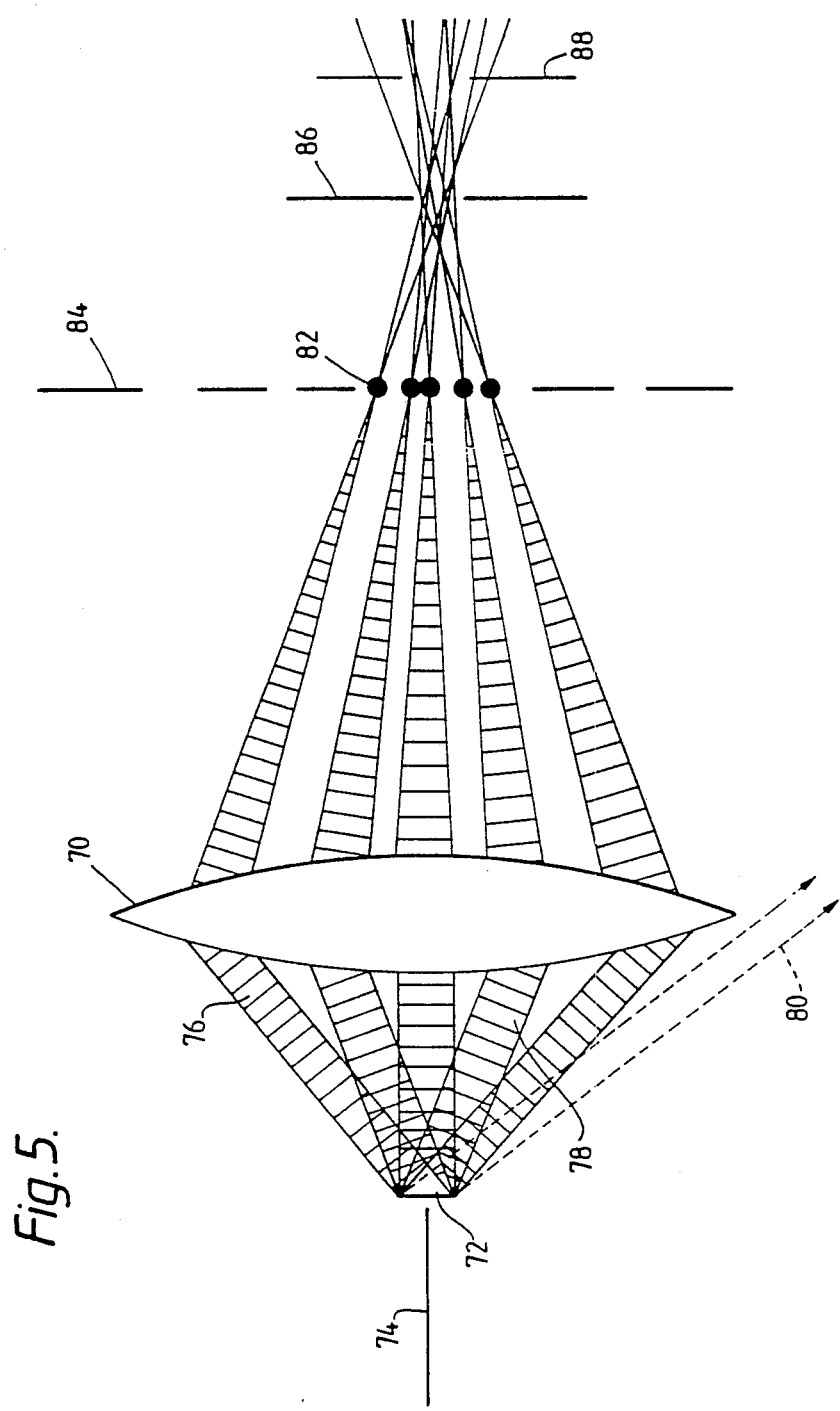
FIG. 5 illustrates Fourier transformation of plane waves into individual spatial modes by a lens.
Figure 6:
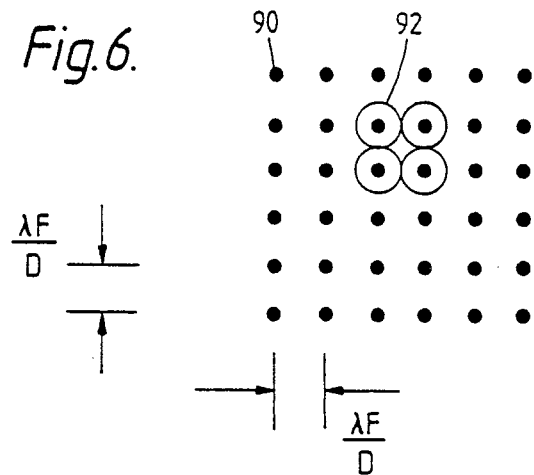
FIG. 6 illustrates individual Airy discs produced by the FIG. 5 lens.

FIGS. 5 and 6 schematically illustrate the Fourier transforming properties of a lens 70. They are described here to clarify the lens-fibre optical coupling employed in FIGS. 1 and 2 to receive scattered light in fibre 34 from the scattering liquid 26. In FIG. 5, the lens 70 receives light from an object 72 disposed on the lens optical axis 74. The light is shown decomposed into plane waves such as 76 and 78 inclined or propagating at a variety of angles to the optical axis 74. Plane waves such as that indicated by a chain line 80 inclined at too great an angle to the axis 74 do not strike the lens 70. This illustrates the operation of a lens as a low-pass spatial filter. It passes only waves of sufficiently low inclination to its optical axis which have correspondingly low spatial frequencies.

The lens 70 transforms each incident plane wave into a small spot such as 82 in its Fourier plane 84, each spot being an Airy diffraction disc. The Fourier plane pattern is shown in FIG. 6. It consists of an array of Airy diffraction discs such as 90 each surrounding by ring systems, of which four first order rings such as 92 are shown. The size of each disc and the disc spacing are determined by the lens diameter D (diffraction aperture size), its focal lenght F and the light wavelength $\lambda$. The spacing is $\lambda F/D$. In accordance with the invention, the receiving or second optical fibre 34 terminates in the Fourier plane 84 and receives light from a single Airy disc. Conveniently the fibre receives the axial Airy disc corresponding to light incident on the lens 70 and propagating parallel to the optical axis 74.

It has been found, surprisingly, that the accuracy of coupling the fibre 34 to a single Airy disc is not particularly critical. This leads to particular ease of optical adjustment to be described later. It arises because a monomode optical fibre transmits only a single spatial mode of light, this being the $HE_{11}$ mode in the form of a plane wave propagating along the fibre axis. Other modes incident on the fibre termination are attenuated as they are transmitted. They become transferred to the fibre cladding where they may be removed easily by known means such as the glue 60 in FIGS. 2 and 3. A monomode optical fibre terminating in the Fourier plane of a light receiving lens accordingly acts as a spatial filter which rejects light other than that originally incident on the lens at a specific angle. It is also greatly beneficial in "cleaning up" a spatially impure laser beam. Spatial coherence defects in a laser beam, such as $TEM_{01}$ and $TEM_{00}$ mixtures, are well known to degrade dynamic light scattering measurements. A monomode fibre attenuates and filters out the unwanted higher order modes, which are undesirably retained in the prior art coherence area approach.

Figure 7:
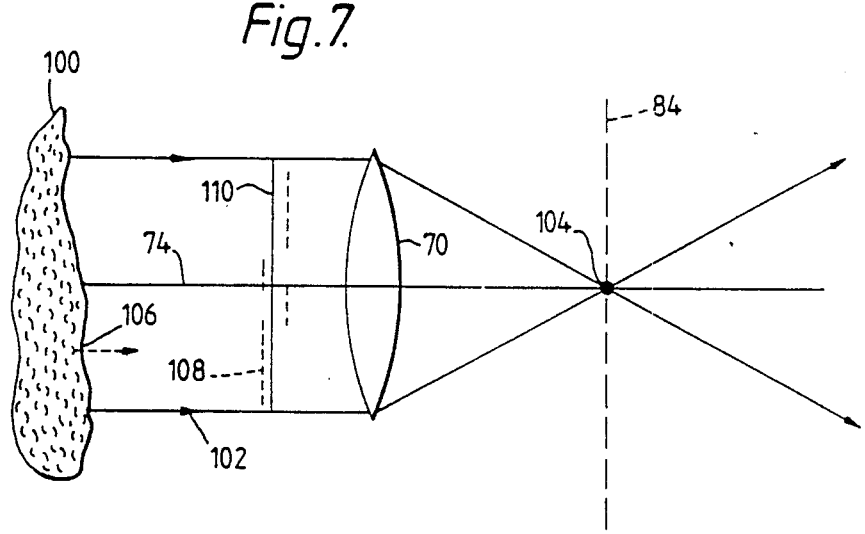
FIG. 7 illustrates phase variation in scattered light incident as a plane wave on the FIG. 5 lens.

Referring now also to FIG. 7, in which parts previously described are like referenced, a scattering liquid volume 100 is shown generating a plane wave 102 propagating along the optical axis 74 of the lens 70. This produces an Airy disc 104 in the Fourier plane 84. All scatterers such as 106 scattering light parallel to the optical axis 74 and incident on the lens 70 contribute to the plane wave 102 and Airy disc 104. The contributions vary in phase as indicated by chain lines such as 108 adjacent an average phase solid line 110. However, this phase variation arises only from path differences along the lens optical axis 74. Mixing of these contributions and consequent interference at the Airy disc 104 accordingly produces intensity fluctuations having a time scale determined by the longitudinal coherence of the scatterers in the volume 100. This coherence is precisely what is required to be determined, since the longitudinal coherence is by definition the temporal coherence or correlation function. Consequently, observation of the intensity fluctuations in the Airy disc of the zero spatial frequency (axial plane wave) component of scattered light yields precisely the temporal correlation function of the scatterers as required for dynamic light scattering measurements. Furthermore, all scatterers in the scattering volume contribute to the axial plane wave, so a very large number of scatterers may be sampled. Alternatively, a large volume containing comparatively few scatterers may be monitored.

Although it is convenient and most optically efficient to detect the zero spatial frequency component of scattered light, it is not essential. If another Airy disc is coupled to the optical fibre, this merely corresponds to a different "look direction" or "squint" of the lens and similar remarks apply. Observation of a different scattering vector is of course involved.

In order to derive maximum benefit from the spatio-temporal properties of a single Airy disc, it is desirable to launch light from it as perfectly as possible into the receiving fibre. In order to achieve this, the Airy disc diameter should be equal to 1.85 times the fibre core diameter (see Optica Acta, Vol. 26, p. 91, 1979, Barrell and Pask). The Airy disc diameter is $2.44\lambda F/D$, where $\lambda$ is the light wavelength and F and D are the lens focal length and diameter. This criterion is equivalent to the Airy disc diameter measured between points $e^{-2}$ times maximum intensity being equal to 1.1 × fibre core diameter, see Optical Fibre Telecommunications, Academic Press 1979. Satisfying this criterion results in the numerical apertures of the fibre and lens being matched. However, it is an advantage of this embodiment of the invention that slightly incorrect matching is not serious. If the fibre numerical aperture is smaller than an Airy disc, power loss results but measurements may still be made. If the reverse is the case, the fibre may accept more than one Airy disc. However, since the fibre transmits only one spatial mode, it is found that only one Airy disc tends to be transmitted and any other is attenuated. Monomode fibres accordingly compensate for reception of more than one spatial mode.

Referring to FIG. 5 once more, for the purposes of comparison the location of typical prior art optical components is illustrated. Instead of Airy disc selection, a typical prior art system employs an image plane optical slit 86 and a pinhole or optical coherence aperture 88 beyond the slit. The lens 70 produces a real image of the scattering volume at the slit 86, which accordingly delimits the scattering volume from which light is received. The coherence aperture 88 restricts greatly the number of scatterers from which light is received. This degrades the statistical properties of the scattered light.

Referring now to FIG. 8, there are shown two plots 120 and 122 of $[g^{(2)}(\tau)-1]$ versus channel number (equivalent to delay time $\tau$). The upper plot 120 was obtained using apparatus of the invention as described with reference to FIGS. 1 to 3. The lower plot 122 was obtained using conventional equipment with considerable care being taken. Both these experiments employed the same sample of polystyrene spheres (0.269 $\mu$m diameter) suspended in water. Moreover, identical laser equipment, detector and detector output processing were employed. The conventional equipment yielded an intercept value of $[g^{(2)}(\tau)-1]$ at $\tau=0$ or zero channel number of 0.64. The equipment for apparatus of the invention is 0.97, an improvement of better than 50%. Moreover, compared to a typical conventional prior art value of 0.4 using average standards of care, the improvement is better than 140%.

Referring to FIGS. 2 and 3 once more, the detailed construction and procedure for assembly of a lens holder 32 is as follows. In one embodiment of the invention, the capillary tube 56 had an internal diameter of 0.15 mm. The fibre 34 had an outer or cladding diameter of 0.12 mm after polymer jacket removal. The lens 30 had a diameter of 3.0±0.2 mm and a focal length of 1.6 mm. The capillary 56 had a diameter 0.1 mm less than that of the hole in the block 58, giving an average radial spacing of 0.05 mm therebetween. As a result, in a worst case the fibre 34 might have its termination or end face misaligned from the lens optical axis by 0.265 mm. This corresponds to an angular deviation from the optical axis of 9.4°, which is unacceptably large. The deviation is reduced to acceptable limits by movement of the lens mount 50 relative to the block transversely of the lens optical axis.

To assemble the lens holder 32 and associated components, the monomode optical fibre 34 is first immersed in sulphuric acid to remove its polymer jacket over about 60 mm of its length adjacent one free end. The exposed fibre cladding is then cleaned in water, and gently scratched near the free end while the fibre is held under axial tension applied by hand. This procedure normally produces a square-cut, clean end-face. The fibre may be scratched or scribed using a diamond-tipped hand-scriber or glass cutter.

The fibre 34 is subsequently threaded into the capillary 56 so that about 1 mm emerges from the capillary's remote end. About 25 mm of unjacketed fibre remains extending from the other capillary end before the polymer jacket begins. This unjacketed fibre region is coated with flexible glue 60 for mechanical retention, stress relief and optical cladding mode stripping as has been mentioned. The fibre-loaded capillary, 56 is then inserted into the brass block 58 and clamped to a micrometer-driven table (not shown), the block 58 being supported independently so that micrometer adjustment results in movement of the capillary through the block.

The lens 30 is then scrupulously cleaned and bonded to its lens mount 50, care being taken to avoid adhesive contaminating the central regions of the lens surfaces. The mount 50 is subsequently assembled with the block 58 by means of the screws 68, which are adjusted to finger tightness permitting the mount 50 to slide on the block.

To adjust for axial alignment of the fibre 34 lens 30, laser light is launched into the fibre's remote end and the output light beam direction is observed. The lens mount 50 is then adjusted by sliding movement on the block 58 until the output laser beam is coaxial with the optical axis of the lens 30. The screws 68 are then tightened.

The separation of the fibre from the lens is then adjusted by micrometer movement. The foregoing setting up procedure has referred to lens holder 32 for convenience, although precisely the same remarks apply to lens holder 20. However, there is an important difference between the lens-fibre separations in the two cases. Lens holder 20 is the light emitting device, and the criterion for the lens-fibre separation is simply that the laser beam waist be formed at a convenient distance, say 5 cm, from the lens 22. The actual distance depends on the scattering volume geometry employed. It is not in fact essential to focus the laser to a beam waist, but for most purposes it is desirable to do so to define the laser beam direction accurately and hence also the light scattering vector.

The beam waist position is adjusted by directing the laser beam on to a ground glass screen arranged at the desired beam waist position. The micrometer is then adjusted to move the capillary and fibre relative to the lens 22 until the laser speckle pattern is seen to "boil", as the expression is in the art. When the laser waist is not at the screen the speckle pattern translates sideways with movement of the screen. When the speckle "boiling" condition is observed, the beam waist is at the correct position and epoxy resin adhesive 62 secures the capillary-block assembly. The fibre end face is now at the image plane of the lens 22 with respect to the beam waist position, the lens-fibre separation being greater than the lens focal length.

The second lens holder 32 is constructed and assembled in a very similar manner to that previously described. The only difference is that the cleaved end face of the second fibre 34 is required to be in or near the Fourier plane of the lens 30, i.e. the lens-fibre separation is required to be substantially equal to the lens focal length. Provided that the Fourier plane of the lens 30 is well separated from its image plane with respect to the laser beam waist produced by the first lens 22, the degree of accuracy of positioning of the second fibre end face is not very critical. The requirement is that the second fibre gather light from one Airy disc or spatial mode as has been said, but the fibre will attenuate other modes. From FIG. 5 it can be seen that this allows a certain amount of positioning tolerance either side of the Fourier plane position. The positioning should sufficiently close to the Fourier plane to meet this requirement.

In practice, the receive fibre adjustment proceeds as previously described, except that the fibre 34 is adjusted relative to the lens 30 so that a laser beam waist is observed at an appreciably more remote distance from the lens than the equivalent for the first lens 22. Strictly speaking the beam waist should be at infinity, but this is not critical. The laser used for adjustment is then removed and the second or receive lens holder 32 is ready for mounting at the same distance from the beam waist in a scattering volume as the first lens holder 20.

It is important to avoid dust particles on the surfaces of the lenses and optical fibre end faces. As regards the end faces and lens surfaces within the lens holders, this may be achieved using clean room assembly techniques. Apart from this, the assembly procedure is little more complex than that required to assemble precision electronic cable terminations, and is well suited to mass production. Once a lens holder is assembled, internal optical surfaces are not exposed to atmosphere and cannot be contaminated with dust. As is well known in optics, dust contamination gives rise to spurious diffraction patterns which produces inaccurate or false measurements in dynamic light scattering in particular.

The monomode optical fibres 18 and 34 may be either polarising or polarisation preserving. These transmit respectively one and two orthogonal polarisation states. To achieve maximum light intensity in the receive fibre 34, it is convenient to mark the capillary support blocks for both fibres with a polarisation direction. In adjustment of a lens holder, the capillary is then rotated while the output laser beam is observed through a polariser. The capillary is then retained in a position which locates beam polarisation parallel to the relevant mark.

Referring now to FIGS. 9, 10 and 11, there are shown schematic drawings of one or more receive fibres coupled via Fourier planes of lenses to laser beam waists. These drawings illustrate the flexibility of use of apparatus of the invention. FIG. 9 (included for completeness and comparison) shows the basic arrangement of a single receive fibre 140 receiving light via a lens 142 from a laser beam waist 144. In FIG. 10, two receive fibres 146 and 148 with respective lenses 150 and 152 monitor a beam waist 154. In FIG. 11 an array of receive fibres and lenses such as 156 and 158 monitor light scattered from a beam waist 160 at a variety of scattering angles. From FIG. 3 it can be seen that the overall length of a lens holder is 53 mm including the glue "tail" 60, or 28 mm without this. Moreover, the block/mount combinations have height and width dimensions of 15 mm×7 mm. In an arrangement such as FIG. 11, their height dimensions will be parallel by comparison with FIG. 2. It is therefore very straightforward to accommodate a number of angularly spaced lens holders within a few centimetres of a scattering volume. This illustrates the vast reduction in bulk or miniaturisation afforded by the invention. Prior art systems equivalent to FIG. 11 would approach a cubic metre in size, whereas the equivalent for the invention is in the order of 20 cm$^3$, an improvement of more than two orders of magnitude.

Referring now to FIGS. 12, 13 and 14, there are shown schematic drawings illustrating use of the invention for homodyne or light beating measurements. In these drawings, lens holders equivalent to 20 and 32 are not shown to simplify illustration. In FIG. 12, light from a laser 170 passes via a launch lens 172 to a monomode optic fibre 174 and thence to a monomode fibre optic coupler 176. Here the light is partly coupled to an output fibre 178 and passes to a beam waist 180. The light is also partly coupled as a local oscillator to a third fibre 182, from which it passes to a second coupler 184 for mixing with light from a receive fibre 186 monitoring scattered light. A detector 188 monitors mixed light output from the second coupler 184.

FIG. 13 shows an extension of the FIG. 12 approach to two scattering angles with a single sample using respective receive fibres 190 and 192. The additional apparatus required apart from the extra receive fibre comprises two additional monomode couplers 194 and 196; one extra coupler 194 is required to divide the local oscillator beam and the other coupler 196 to mix the second receive fibre signal. An additional detector 198 monitors the output of the coupler 196.

FIG. 14 illustrates use of the invention in conjunction with two different scattering volumes. It differs from FIG. 13 in that it incorporates an extra monomode coupler 200 to direct light to a second beam waist 202 in a different sample, and in that receive fibres 204 and 206 collect light from different waists.

The FIGS. 13 and 14 arrangements extend naturally to larger number of scattering angles and samples. The use of monomode optical fibres for homodyne or heterodyne measurements has a specific and very important advantage over the multimode fibre apparatus of Auweter and Horn previously described. Light propagates along the core of a multimode fibre as a TEM$_{00}$ plane wave having a wavefront perpendicular to the fibre axis. Mixing a monomode coupler produces the ideal required for light beating measurements, this being the superposition in the same plane of two waves having the same spatial mode or frequency. In contradistinction, multimode fibres propagate waves at a plurality of angles to the fibre axis. Mixing of two such beams produces interference between different modes which are imperfectly superimposed. Furthermore, and very importantly, mechanical vibration of multimode fibres in light beating arrangements changes the intermode mixing. In other words, mode A beating with with mode B changes to beating with mode C of different amplitude. More complex changes can of course occur. The result is that mechanical disturbance of multimode fibres may easily produce discontinuous changes in the amplitude of the beat signal, rendering measurements valueless. The use of monomode fibres for light beating measurements in accordance with the invention is therefore fundamentally less sensitive to mechanical disturbance than the multimode prior art alternative.

Multi-sample measurements as illustrated in FIG. 14 are potentially very important in medical science for measurements on biological specimens such as urine, and also in biotechnology for monitoring fermentation processes and the like. Conventional equipment is entirely impractical for measurements of this kind.

Referring now to FIG. 15, there is shown a simplified embodiment of the invention. Laser light is scattered from a scattering volume 210 via an interference filter 211, an aperture 212 and a lens 213 to a Fourier plane aperture 214 matched to an Airy disc of the lens. A photodetector 216 is arranged to receive light from the aperture 214. The photodetector 216 accordingly detects a single spatial mode of light from the scattering volume 210 provided that the aperture 214 transmits light from no more than a single Airy disk. The size and positioning of the aperture 214 are therefore more critical than is the case when a monomode fibre is employed to relay light, since the spatial filtering properties of such a fibre are not employed. The detector 216 and aperture 214 shou,d be coplanar, so that the angular diffraction spectrum from the aperture 216 is not allowed to develop by divergence beyond it.

However, in the emerging field of integrated optoelectronics this need not necessarily be a serious limitation. Conventional gas lasers and photomultiplier tube detectors are presently being replaced by considerably smaller semiconductor lasers and avalanche photodiode detectors. These offer further scope for component miniaturisation and cost reduction.

Referring now to FIG. 16, there is schematically shown an embodiment 220 of the invention suitable for production by integrated techniques. A substrate 222 supports a semiconductor laser 224 with superimposed lens 225 and an avalanche photodiode 226. The photodiode 226 is surmounted by an aperture 228. A layer 230 transparent to radiation from the laser 224 surmounts the aperture 228 and supports a lens 232. The aperture 228 is located accurately in the Fourier plane of the lens 232. The device 220 is employed in combination with a sample cell 234 having one wall configured as a prism 236. This reflects laser light 238 along a path 240, and light is scattered at 90° in a direction 242. The device 220 may be bonded to or encapsulated with the cell 234.

If the photodiode 226 has photosensitive surface region equal to or less than an Airy disc, the aperture 228 is unnecessary. Moreover, for light measurements near 180° (backscattering), the prism 236 may be dispensed with.

The device 220 may be constructed by known lithographic techniques. Since laser/photodiode pairs are generally of dissimilar semiconductor materials, the substrate 220 may require additional layers to permit growth of different materials on different surface regions. This is however known technology and will not be described. The lenses 225 and 232 may be produced by selectively etching a sufficiently wide band gap semiconductor material, as described in British Patent Appln. No. 8511064 for example.

The device 220 requires only electrical connections (not shown) to supply electrical current to the laser 224 and to apply bias voltage to and output photon detection pulses from the photodiode 226. Some (but not all) conventional avalanche photodiodes require bias voltages in excess of 200 V, which may be inconveniently large for the purposes of integrated circuit design. If detection considerations warrant use of a high voltage photodiode, the integrated photodiode 226 might be replaced by an integrated optical waveguide coupled to a monomode optical fibre. The fibre would transmit light to a remote conventional photodiode as previously described.

The device 220 has the advantage of being within the manufacturing scope of integrated circuit production techniques. These are easily capable of the required optical alignment accuracy, and offer a potentially cheap method of production. Moreover, the device 220 may be constructed in a form suitable for dipping in a liquid. This merely requires the device to be constructed in encapsulated form with scattering liquid allowed to communicate with the interior of the cell 234. Use of such a cell is not essential, since it merely defines a scattering volume. Some applications of the invention may employ an optical head having two mutually inclined walls, light emerging from one wall and being scattered to the other and the region partly bounded by the walls being otherwise unenclosed. Moreover, in backscattering measurements only a single wall is required.

Encapsulation of the device 220 and its variants described above provide the advantage of a high degree of immunity from dust particles which render measurements inaccurate or valueless. An encapsulated device assembled under clean room conditions can only suffer from dust contamination on the walls of the cell 234 or the equivalent for devices not employing a fully enclosing cell. Conventional optical systems possess a multiplicity of surfaces all of which must be kept scrupulously clean.

Referring now to FIG. 17, there is schematically shown an embodiment of the invention indicated generally by 250 and suitable for laser Doppler difference velocimetry. The velocimeter 250 comprises a laser 252 providing an output 254 divided into two beams 256 and 258 by a beam splitter 260. The beams 256 and 258 pass through a phase modulator 262. Two mirrors 264 provide a relative beam displacement sufficient to allow the beams to be launched into separate fibres 266 and 268 by microscope objectives 270 and 272. The fibres 266 and 268 terminate in lens holders 274 and 276 as described with reference to FIGS. 2 and 3. The lens holders produce superimposed beam waists at 278 in a flow of gas indicated by an arrow 280, and two further arrows 282 and 284 indicate beam directions. A receive lens holder 286 collects light 287 scattered from the scattering volume 278 for subsequent photodetection, correlation and computer numerical analysis at 290, 292 and 294 respectively.

Turbulence in the gas flow 280 is investigated by means of monitoring fluctuations in the fringe patterns produce by the interfering beams at 278. The principles of laser Doppler velocimetry are well known and will not be described further.

If it is required to investigate and possibly correlate different light scattering spatial modes simultaneously, a monomode fibre optic bundle and lens may be employed. The bundle is arranged with each fibre end face in the lens Fourier plane, and each fibre transmits a respective Airy disc. The output of each fibre is then monitored separately.

Hitherto the use of conventional-albeit miniaturised-lenses has been described for the purposes of producing a spatial Fourier transform of scattered light. More generally, any optical means may be employed to achieve this provided that individual Airy discs are produced from which one spatial mode may be isolated. The isolation procedure may require spatial filtering with a monomode optical fibre. Alternatives to conventional lenses do however exist. These include graded refractive index lenses of cylindrical form in which the refractive index reduces from a maximum at the cylinder axis to a minimum at its curved surface. One commercially available graded index lens variety employs a tubular lens mount within which the lens is arranged coaxially. This type of lens is particularly convenient to use in combination with monomode fibres, since the tube internal diameter is matched to the fibre cladding diameter. The fibre is simply moved along the tube until its end face or termination is the correct distance from the lens.

A further alternative known focussing or Fourier transforming means comprises tapering the end of a monomode optical fibre to a sharp point of dimensions much less than the fibre core. The point should be arranged to be on or close to the axis of the core. This produces focussing properties akin to those of a lens. At present it is difficult to control focal length accurately, and it is necessary to select tapered fibres of the correct optical properties from a prepared batch. The situation may improve in future. It is however possible to use taper ended monomode fibres without other focussing means both to illuminate the scattering fluid and to collect scattered radiation.

The invention may also employ holographic focussing devices of known kind for the purposes of fluid illumination and spatial mode selection from scattered light. Moreover, whereas transmissive optics have been described, their reflecting equivalents may also be employed.

What is claimed is:

1. A dynamic light scattering apparatus comprising a laser (12) arranged to produce a laser beam (24) in a fluid scattering volume (26), and means (28 to 36) for collecting and detecting light scattered from the scattering volume (26), characterised in that the apparatus (10) also includes means (30, 34) for spatially Fourier transforming light scattered from the scattering volume (26) and for isolating a single spatial mode thereof for detection.

2. A dynamic light scattering apparatus according to claim 1 characterised in that the Fourier transforming and isolating means comprises focussing means (30) and aperture defining means (34) arranged to transmit light from a single Airy disc (82) of the focussing means (30) to detecting means (36).

3. An apparatus according to claim 2 characterised in that the focussing means comprises a lens (30) and the aperture defining means comprises an end face of a monomode optical fibre (34), the fibre (34) being arranged to attenuate unwanted spatial modes.

4. An apparatus according to claim 1 characterised in that it includes monomode fibre optic coupling means (176) arranged to mix scattered and unscattered laser light as required for light beating measurements.

5. An apparatus according to claim 1 characterised in that the laser (224) and the Fourier transforming and isolating means (228, 230, 232) are produced by integrated techniques on a common support (222).

6. An apparatus according to claim 5 characterised in that the Fourier transforming and isolating means (228, 230, 232) comprises a lens (232) and a photodiode (226) arranged to receive light from a single Airy disc (82) of the lens (232).

* * * * *